United States Patent
Baer et al.

(10) Patent No.: US 9,243,984 B2
(45) Date of Patent: *Jan. 26, 2016

(54) METHOD AND APPARATUS FOR THE SIMULTANEOUS, AUTOMATED DECOMPOSITION OF A PLURALITY OF BIOLOGICAL SAMPLES

(75) Inventors: Gerhard Baer, Illingen (DE); Dennis Mertens, Hilden (DE); Andreas Schaefer, Leverkusen (DE); Friederike Wilmer, Koenigswinter (DE)

(73) Assignee: QIAGEN GMBH, Hilden (DE)

( * ) Notice: Subject to any disclaimer, the term of this patent is extended or adjusted under 35 U.S.C. 154(b) by 834 days.

This patent is subject to a terminal disclaimer.

(21) Appl. No.: 13/063,805

(22) PCT Filed: Aug. 6, 2009

(86) PCT No.: PCT/EP2009/060173
§ 371 (c)(1),
(2), (4) Date: Jun. 30, 2011

(87) PCT Pub. No.: WO2010/031636
PCT Pub. Date: Mar. 25, 2010

(65) Prior Publication Data
US 2011/0281259 A1  Nov. 17, 2011

(30) Foreign Application Priority Data
Sep. 18, 2008 (EP) ................................ 08164548

(51) Int. Cl.
*B02C 19/00* (2006.01)
*B02C 17/14* (2006.01)
(Continued)

(52) U.S. Cl.
CPC ............... *G01N 1/286* (2013.01); *B02C 17/14* (2013.01); *B02C 19/00* (2013.01); *G01N 1/42* (2013.01); *G01N 2001/2866* (2013.01)

(58) Field of Classification Search
CPC ........ B02C 19/00; B02C 17/14; B02C 17/18; B02C 19/186; A47J 19/06; C12M 1/02; C07H 1/00; C12Q 1/68; G01N 1/286; G01N 1/42; G01N 2001/2866; B01L 3/502
USPC ............. 241/2, 23, 30, 65, 66, 172, 175, 176, 241/283, 30.2; 435/173.7
See application file for complete search history.

(56) References Cited

U.S. PATENT DOCUMENTS
4,295,613 A * 10/1981 Moore et al. ...................... 241/2
5,464,773 A * 11/1995 Melendez et al. .......... 435/306.1
(Continued)

FOREIGN PATENT DOCUMENTS
DE  738286  8/1943
DE  10153957  11/2001
(Continued)

OTHER PUBLICATIONS
SPEX CertiPrep Group L.L.C. "SPEX SamplePrep 2010 Geno/Grinder® demonstration video" (Aug. 28, 2009) available at http://www.youtube.com/watch?v=-QFEO1QpTPU.
(Continued)

Primary Examiner — Faye Francis
Assistant Examiner — Onekki Jolly
(74) Attorney, Agent, or Firm — Miles & Stockbridge PC

(57) ABSTRACT

The invention relates to a method for decomposing a biological sample (9), the method having the following steps: the sample (9) is put into a container (6) which is composed of plastic, in particular, the container (6) is inserted into an adapter (2, 2a), the adapter with the closed container therein is connected to an apparatus which moves the adapter back and forth, in particular upwards, in automated fashion. This method makes it possible to decompose biological samples in automated fashion, to be precise both samples at room temperature and frozen samples. The invention also relates to an apparatus for carrying out the method, the apparatus having an adapter (2, 2a) which is predominantly composed of plastic and has sleeves (4) which are composed of metal and are intended to accommodate containers (6) which are composed of plastic, in particular.

20 Claims, 2 Drawing Sheets

(51) Int. Cl.
  *G01N 1/28* (2006.01)
  *G01N 1/42* (2006.01)

(56) References Cited

U.S. PATENT DOCUMENTS

| | | | | |
|---|---|---|---|---|
| 5,707,861 | A | * | 1/1998 | Sherman et al. ............ 435/306.1 |
| 5,921,477 | A | * | 7/1999 | Tomes et al. ....................... 241/2 |
| 6,235,501 | B1 | | 5/2001 | Gautsch et al. |
| 6,498,037 | B1 | * | 12/2002 | Carey et al. ....................... 436/50 |
| 6,706,498 | B2 | * | 3/2004 | Gautsch et al. ............. 435/91.1 |
| 6,739,531 | B2 | * | 5/2004 | Taylor ................................ 241/1 |
| 7,337,998 | B2 | * | 3/2008 | Melton et al. .................. 241/100 |
| 7,467,754 | B2 | * | 12/2008 | McCambridge et al. ......... 241/2 |
| 7,785,868 | B2 | * | 8/2010 | Yuan et al. ................. 435/306.1 |
| 7,954,741 | B2 | * | 6/2011 | Kunc et al. ....................... 241/65 |
| 8,016,218 | B1 | * | 9/2011 | Friedman ...................... 241/175 |
| 8,020,790 | B2 | * | 9/2011 | Kemppainen et al. ............. 241/2 |
| 8,348,183 | B2 | * | 1/2013 | Mertens et al. .................... 241/2 |
| 2004/0035964 | A1 | * | 2/2004 | Roggero ....................... 241/169 |
| 2004/0115720 | A1 | | 6/2004 | McWilliams et al. |
| 2004/0132082 | A1 | * | 7/2004 | Gautsch et al. .................... 435/6 |
| 2004/0144874 | A1 | | 7/2004 | Moskowitz |
| 2005/0089859 | A1 | | 4/2005 | Singer et al. |
| 2005/0178726 | A1 | | 8/2005 | Belly et al. |

FOREIGN PATENT DOCUMENTS

| | | |
|---|---|---|
| DE | 602005001256 | 6/2006 |
| EP | 1577011 | 9/2005 |
| EP | 1674008 | 6/2006 |
| JP | 03-186360 | 8/1991 |
| JP | 2002066366 | 3/2002 |
| JP | 2006051505 | 2/2006 |
| WO | 2004082837 | 9/2004 |

OTHER PUBLICATIONS

Letter dated Feb. 3, 2011 from Retsch GmbH to Qiagen GmbH in German and translation of letter into English.
International Search Report for PCT/EP2009/060173, mail dated Sep. 25, 2009 (4 pages).

* cited by examiner

METHOD AND APPARATUS FOR THE SIMULTANEOUS, AUTOMATED DECOMPOSITION OF A PLURALITY OF BIOLOGICAL SAMPLES

CROSS REFERENCE TO RELATED APPLICATIONS

This application is a §371 National Stage Application of PCT/EP2009/060173 filed Aug. 6, 2009, which claims priority to European Application 08164548.3 filed Sep. 18, 2008.

BACKGROUND OF THE INVENTION

1. Field of the Invention

The invention relates to a method and a device for disrupting a plant or animal sample for processing, i.e. for example the isolation of nucleic acids or proteins from the sample. Such preparations and tests are performed in a laboratory by a laboratory technician in accordance with standardized processing instructions. A so-called protocol is a part of such processing instructions. An example of such a protocol for isolating plasmid DNA from E. coli is apparent from document DE 101 53 957 A1.

2. Description of Related Art

In order to process a sample in the desired manner, i.e. isolate the nucleic acids or proteins, for example, so-called "kits" are commercially available depending on the sample and the desired result, such as the "UltraClean Tissue DNA Isolation Kit" by Qiagen (www.Qiagen.com). Prior to processing a sample using such a kit in accordance with a pre-defined protocol, the sample has to be prepared in a suitable manner.

Such typical preparations known from the prior art are being described below.

For example, an organ is removed from a laboratory animal, e.g. a rat. The selection of the organ of the animal depends on the objective. The removed organ or tissue of the animal is washed in a wash buffer solution such as in PBS (Phosphate Buffered Saline, with the following contents: $Na_2HPO_4$ (dried), $NaH_2PO_4$ (dried), NaCl and distilled water). Due to the washing process, the tissue of the removed part is provided in a blood-free state and is freed from undesired components.

Then, the removed tissue is cooled in liquid nitrogen, in order to stop cellular activities, among other things. Otherwise, the desired information would not be obtained in the desired quality subsequent to processing. Typically, tissue having a body temperature of, for example, 37° C. is submerged in liquid nitrogen in the process. Bubbles will develop. The tissue is withdrawn from the liquid nitrogen not until the formation of bubbles ceases. The tissue is then stored at −80° C. using, for example, dry ice.

If the cooling step in liquid nitrogen is to be avoided, then, as an alternative, the removed tissue is chemically preserved subsequent to the washing process, using stabilizing reagents such as RNAlater®, for example. RNAlater® is a viscous liquid which was developed by the company Ambion (www.ambion.com) for preserving fresh tissues. The preservative effect is primarily based on all enzymes being inactivated in the tissue by the removal of water, and on cellular activities being stopped. The viscous liquid has to diffuse quickly into all cells of the tissue. Therefore, the size of the pieces of tissues has to be limited to a side length of half a centimeter at most. Subsequent to the chemical treatment, the tissue thus treated is also cooled at −80° C. in order to store it thus until processing.

Typically, 10 to 100 mg of tissue is required for processing in order to be able to perform the desired test, isolation or the like. Prior to processing, the required amount of animal tissue is cut off using a scalpel, for example.

Individually or in combination, the sample preparation steps mentioned so far can be features of the invention described below.

The cut sample, that is, the cut tissue, is now disrupted, meaning that the cell walls have to be opened. This can be done mechanically, chemically or enzymatically. Mechanical disruption is carried out, for example, using a "TissueRuptor" by the company Qiagen, known from the TissueRuptor Handbook, July 2006, by Qiagen, Hilden Germany. In this case, a rotating blade disintegrates the cell walls of the tissue at 35,000 revolutions per minute. As a rule, mechanical disruptions are being carried out in a buffer in order to avoid damage to the ingredients, such as nucleic acids.

A mechanical disruption carried out in a container in the presence of a buffer, that is, a chemical substance, is known from document EP 1577011 A2.

Preparing samples in a cryogenic mill is also known (see for example http://www.laborpraxis.de/fachartikel/lp_fachartikel_nh_2384859.html, Mar. 12, 2007). In this actively cooled mill, the sample is ground at the temperature of liquid nitrogen. The sample remains deep-frozen during the entire grinding process without coming into contact with the nitrogen. This technically quite complex method can be carried out in the case of such samples in which the above-mentioned method fails, for example in the case of very hard materials, such as bone, or of collagen-containing materials, such as skin. If a bone is to be prepared, putting it into a vessel filled with liquid nitrogen and crushing it using a metallic pin is also known. The bone is subsequently provided in a powdered form.

If histological tests with a microscope are to be carried out, then a sample is first impregnated with paraffin, hardened, and then cut into thin layers of tissue using a microtome.

If plant samples are to be processed, cutting them to size with a scalpel is only possible in the case of soft materials, such as leaves, soft beans etc. In the case of dried or frozen plant samples, they are frozen in liquid nitrogen and ground using a pestle in a mortar actively cooled with liquid nitrogen.

The German patent specification 738 286 teaches freezing and grinding cells together with a dispersion liquid in order thus to disintegrate the cells.

A crushing/mixing device for foodstuffs such as spices is apparent from each of the documents DE 602005001256 T2 and WO 2004/082837 A1. The device comprises a hollow body with a ball placed therein with which foodstuffs are to be crushed.

Documents US 2004/0144874 A1, JP 2006051505 A, JP 2002-066366 A and JP 03-186360 A disclose other examples for ball mills and comparable devices. No method for disrupting a biological sample is apparent from these documents.

SUMMARY OF THE INVENTION

A preparation of the samples in the above-mentioned manner pursues the aim of obtaining as good as a sought-for result as possible subsequent to processing. Accordingly, it is an object of the present invention to disrupt a biological sample suitably and simply.

A solution of the object comprises the features of claim 1. A device for carrying out the method comprises the features of the independent claim. Advantageous embodiments are apparent from the dependent claims.

DETAILED DESCRIPTION OF A PREFERRED EMBODIMENT

Figure 1:
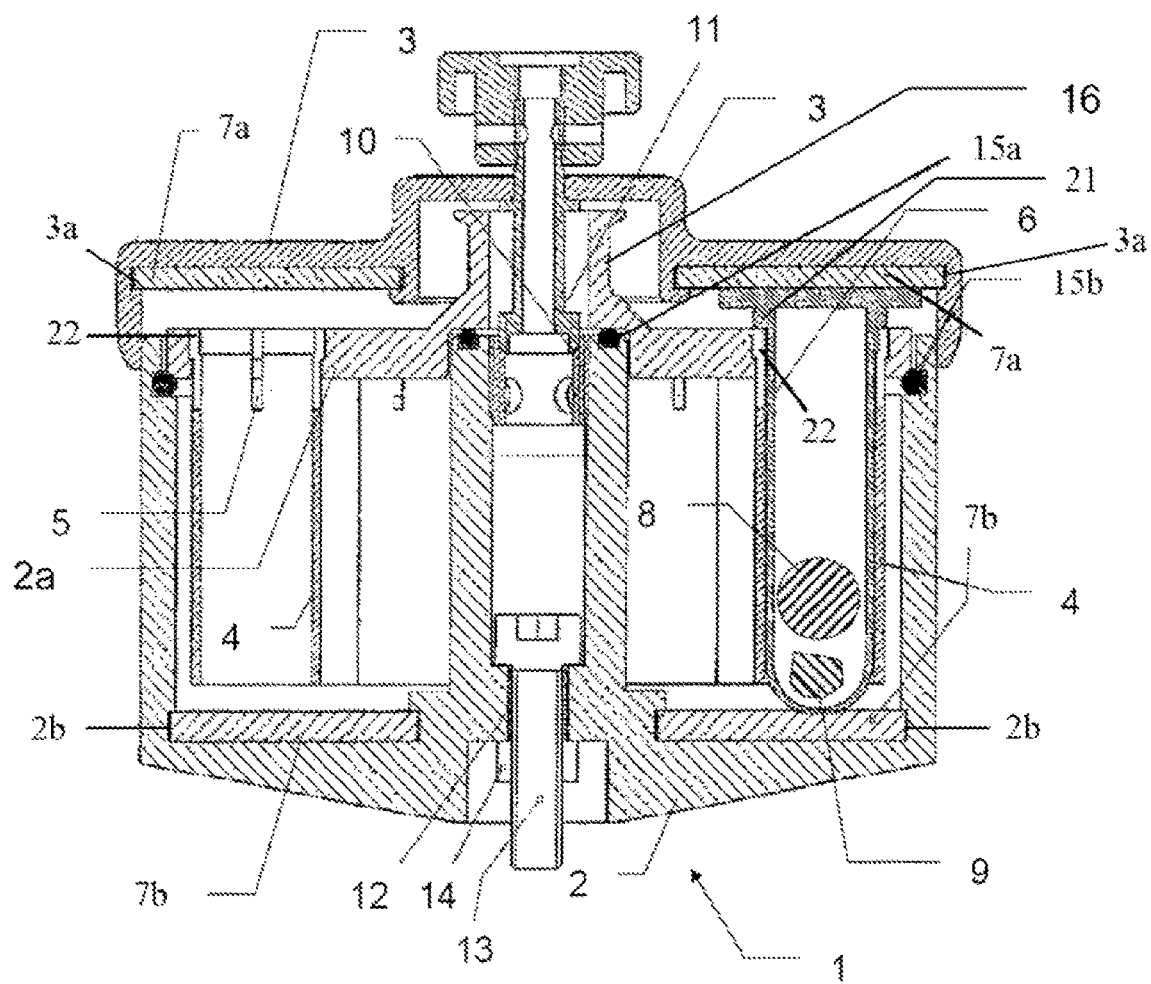
FIGS. 1 and 2 describe embodiments of the present disclosure.

A suitably prepared sample is inserted into a container consisting of plastic. The plastic container is inserted into an adapter. The plastic container is then sealed. It can have been sealed by the lid of the adapter. Preferably, however, the plastic container has its own lid, so that the plastic container is sealed even if it is removed from the adapter subsequent to the disruption process. Moreover, the effort for cleaning is thus minimized if the plastic container is not reused but ultimately disposed of. The adapter is in turn connected to an apparatus that automatically reciprocates the adapter, in particular up and down, in order to thus disrupt the sample. In particular, the adapter is configured in such a way that it is capable of accommodating a plurality of plastic containers in order to be able to disrupt a plurality of biological samples simultaneously.

A sample is suitably prepared prior to insertion into the plastic container in particular by the sample first being washed and then preserved, either using liquid nitrogen or chemically, that is, for example using RNAlater® by the US company Ambion, Foster City, or using AllProtect by Qiagen according to the webpage http://www1.qiagen.com/products/RnaStabilizationPurification/AllprotectTissueReagent.aspx. Primarily depending on the size of the plastic container, the suitably prepared sample is entirely or partially filled into the plastic container. If only a part of the sample is filled in, then this part is cut off by means of a scalpel, for example.

Since, in the case of chemical preservation, a sample to be preserved has to be small, the plastic container is preferably dimensioned such that it is only capable of accommodating small samples. Therefore, if there are always only small sample quantities of preferably no more than 50 mg, particularly preferably of no more than 30 mg to be prepared for this reason, handling errors are thus avoided in an improved manner.

The method enables an automated disruption of samples, namely in various ways. By first putting the frozen or chemically preserved sample into a plastic container which in the inserted state is sealed, a contamination of other constituents of the overall device is thus avoided. The plastic container is an inexpensive disposable article which, after the sample has been disrupted, does not have to be reused due to reasons of economy. Cleaning the used plastic container can therefore be dispensed with. Since the adapter is capable of accommodating a plurality of plastic containers with a sample located therein, a plurality of samples can then be disrupted simultaneously.

Fundamentally, the adapter, on the other hand, is an item that is separate from the apparatus in order to be able to prepare the adapter suitably and simply. In particular, it is easily possible in that case to cool the adapter prior to the insertion of the plastic containers with the samples in a temperature range of, in particular, −20° C. to −80° C., for example in a refrigerator or by using dry ice, in order thus to be able to disrupt a frozen sample without having to fear that the sample will thaw, despite a lack of active cooling.

The teaching according to the claims works both for plant as well as for animal or human tissue, both for stabilized as well as for fresh samples of plants or tissues. Furthermore, disruption is possible in a very simple manner both at room temperature, for chemically preserved samples, as well as for frozen samples at low temperatures.

In order to be able to reliably keep a frozen sample suitably cool during disruption, the adapter, in one embodiment, comprises one, preferably several metallic casings that are inserted into the plastic containers. Beyond that, the adapter consists entirely or at least predominantly of plastic. Metallic casings have the heat capacity required for keeping the plastic container cool over a sufficient length of time. Furthermore, the adapter consists entirely or at least predominantly of plastic so that the adapter does not become too heavy, which would make handling it much more difficult.

In one embodiment of the invention, a deep-frozen sample is put into a cooled plastic container which additionally contains at least one moveable hard body. The cooled plastic container is then inserted into the cooled adapter or the metallic casing of the cooled adapter. The temperature to which the adapter is cooled in one embodiment should be lower than −50° C. in order to reliably prevent the frozen sample from thawing during disruption. Preferably, a temperature of approx. −80° C., for example of from −70° C. to −90° C. should be selected. −80° C. or −70° C. to −90° C. can be provided in a cost-effective manner using dry ice or in a refrigerator. It was found that particularly good results can be obtained by cooling down to approx. −80° C. Temperatures lower than −80° C. are possible to a certain degree. However, attention should be paid to the fact that the adapter must not be cooled off too much in order to carry out the disruption. For example, the temperature of liquid nitrogen, that is −196° C., has proven too low to obtain good results. Then, after insertion into the apparatus, the adapter is reciprocated very quickly so that the moveable body is shaken, relative to the plastic container, in such a way that the deep-frozen sample is crushed and disrupted by the moveable body. An additional active cooling of the adapter, for example by means of nitrogen, has proved to be unnecessary and is therefore preferably not provided. This makes handling considerably easier compared with the prior art, which requires an active cooling during the disruption process.

A cylindrical interior of the plastic container with at least one hollow-sphere-shaped end is particularly suitable. In that case, the moveable body is preferably a ball or a pin having spherical ends. The diameter of the ball or of the pin is slightly smaller than the diameter of the interior of the plastic container in order thus to ensure mobility. The moveable body consists of a hard, preferably heavy material, such as metal, in order to be able to crush the sample. The sample is preferably introduced into the plastic container in such a way that it is placed between a hollow-sphere-shaped end of the plastic container and the ball or pin. The diameter of the ball or pin is preferably at least 5 mm, particularly preferably at least 8 mm. The diameter of the plastic vessel is preferably no more than 15 mm, preferably up to 10 mm. Preferably, the plastic container is arranged vertically during the disruption process, and the hollow-sphere-shaped end is at the bottom. Owing to gravity, the sample material remains primarily in the lower region so that just one (lower) hollow-sphere-shaped end suffices for crushing reliably using a ball.

In particular, a sample that is at least −50° C. cold is put into the plastic vessel. The vessel is then shaken for, in particular, 10 to 200 seconds using the apparatus in such a way that the moveable body is thrown back and forth, preferably up and down, preferably at a frequency of 10 to 100 Hz, in particular at a frequency of at least 30 Hz. If shaking or reciprocating goes on too long, the sample threatens to thaw. In order to be able to reliably disrupt the sample within the available time, the reciprocating process has to be sufficiently long and at a sufficiently high frequency. The sample thus crushed can then be removed from the plastic vessel and the desired quantity can be processed using a kit, in accordance with a protocol. Apart from the frozen sample and one or more moveable hard bodies, there are then basically no other substances in the vessel, in particular no cooling agent, such as liquid nitrogen or, for example, buffer solutions. They would, at least in the usual case, only adulterate the desired result.

Surprisingly, it was found that very good results are obtained with this form of disruption of a frozen probe, in comparison with the sample preparations known from the prior art, even though no great technical effort is being made and handling is simple. A disruption in, for example, a TissueRupter can be or is dispensed with, since this additional disruption is basically not necessary. The sample thus prepared can therefore be processed immediately, and with particularly good results. The technical effort is not large because the vessel with the moveable body and adapter located therein is only cooled, for example in a refrigerator, to a temperature of, for example, −50° C. to −80° C. After the sample has been crushed, it can be removed and, for example, be stored cooled in another vessel for the time being. Alternatively, the sample is not removed and stored in another vessel, but right away in the plastic vessel containing the moveable body. In that case, it thus serves both as a disruption container and a storage container. The desired sample quantity for processing can be made available accurately and simply. In addition, a homogeneous tissue distribution is achieved in the process. Even stabilized tissue, leaves and seeds of plants can be prepared for further processing in this way. However, this method is not suitable for skin and bones and comparably hard or viscous samples.

Since the treatment in the cooled, sealed adapter does not require much time, it is not necessary to interrupt the shaking process and cool the adapter down to suitably low temperatures in the interim. This applies particularly if the adapter has casings of metal with walls of sufficient thickness. As a rule, a wall of a few millimeters thickness is already sufficient. In one embodiment, the thickness of the wall is at least 0.5 mm in order to provide for a sufficient heat capacity, preferably at least one millimeter. In order not to become too heavy, the wall in one embodiment is no more than 4 mm.

Since after crushing, the sample is provided in powder form, it advantageously has a particularly large surface area on which subsequently used chemicals can act. A desired quantity of powder can be provided for subsequent steps in a particularly simple manner, for example by weighing or even by correspondingly dimensioned measuring vessels, such as a measuring spoon.

The adapter is itself suitable for disrupting a non-cooled sample in a non-cooled state. However, the sample is in that case disrupted by means of a lysis buffer which is located in the plastic container together with the sample during the disruption process. The sample can also be crushed when the adapter is used non-cooled. In this case, a solution of the buffer and the tissue is produced. Suitable lysis buffers include buffers comprising complexing agents and surfactants for disrupting DNA, such as, for example, the lysis buffer ATL, commercially available from Qiagen GmbH, Hilden, Germany, or buffers comprising a chaotropic agent for disrupting RNA, such as, for example, the lysis buffer RLT, commercially available from QIAGEN GmbH.

After the previously weighed-in pieces of tissue have been processed into a powder in the cooled state, a buffer is added in one embodiment, i.e. the powder is transferred into solution. Difficulties are thus avoided in order to again remove very small sample quantities of, for example 10 mg tissue powder.

If tissue is disrupted, relatively large metallic moveable bodies located in the plastic containers are preferably used for disruption. If bacteria are disrupted, then the moveable, relatively small bodies consist, in particular, of glass (so-called glass beads). Glass beads have a small diameter and are like sand. Friction thus becomes very much stronger. These properties are required in order to be able to disrupt bacteria. As a rule, metallic beads are too large so that the distance between the individual spheres would offer too much clearance to be able to thereby disrupt bacteria.

Instead of the above-mentioned plastic, a different non-metallic material can, in principle, also be selected, in particular if it is comparable to plastic. However, plastic is to be particularly preferred.

Other advantages and embodiments become apparent from the following descriptions of experiments.

FIG. 1 shows a lateral section through an adapter 1. The adapter 1 comprises a container-shaped basic body 2 that has been sealed with a lid 3. In the basic body, a total of twelve casings 4 consisting of aluminum are disposed in a circle about a central axis of the adapter. The wall thickness of the casings 4 is 1 mm. The casings 4, in their upper area, have one or more slots 5. The upper area with the slot is clampingly retained in an annular insert 2a located in the basic body 2. The casings 4 can therefore be removed from the basic body 2 for cleaning purposes, particularly easily together with the annular insert 2a.

FIG. 1 shows a plastic container 6 provided with a lid and inserted into a metallic casing 4. The plastic container 6 is clamped between two elastic annular discs 7a & 7b of foamed silicone disposed below and above the plastic container 6. The upper annular disc 7a is held by the lid 3 by means of lateral grooves 3a disposed on the underside of the lid 3. The lower annular disc 7b is held on the bottom of the basic body 2 by lateral grooves 2b. The elastic discs 7a & 7b stabilize the container during the disruption process, so that it cannot be damaged. Furthermore, the elastic discs 7a & 7b have a noise-reducing effect.

The bottom of the container 6 consisting of plastic is hollow-sphere-shaped. A ball 8 consisting of steel is located in the container 6. A biological sample 9 is placed between the steel ball 8 and the hollow-sphere-shaped bottom of the plastic container 6. It is enough that only the bottom, and not also the lid area, of the plastic container 6 is hollow-sphere-shaped because, owing to gravity, the sample will remain at least predominantly in the lower portion so that the sample is crushed in the bottom area.

In its upper half, the basic body 2 is provided with a steel thread insert 10 into which a fastening screw 11 of the lid 3 is screwed in order to seal the basic body with the lid. A quarter turn preferably suffices for fastening the lid. There is, in the bottom half, a further steel threaded bushing 12 into which a screw 13 has been screwed so that the thread of the screw 13 protrudes over the bottom area of the container 2. Moreover, the screw 13 is fastened with glue and countered with a nut 14 so that it can be relied on not to become detached from this fastened state.

The portion of the thread of the screw 13 protruding downwards serves for detachably fastening the adapter 1 to the apparatus with which the adapter is moved up and down in an oscillating manner in order thus to crush a sample 9 with a ball 8 and disrupt it.

Moreover, the basic body 2 consists of plastic, namely of polyoxymethylene. This plastic withstands low temperatures of about −80° C. as well as common cleaning solutions. The annular insert 2a consisting of polyoxymethylene is supported, in the upper area of the basic body 2, by O-rings 15a & 15b of silicone with a hardness of 50 Shore and furthermore clampingly retained by the lid 3. The upper area of the metallic casings is clamped into the annular insert 2a. The rings consisting of silicone thus serve for reducing noise. However, other plastics that meet the above-mentioned requirements may also be chosen.

The lid 3 and the annular insert 2a can be separated from each other by an elastic intermediary layer in order thus to further reduce noise during disruption. The intermediate layer can also be a silicone ring.

The annular insert 2a comprises an upwardly protruding, centrally disposed grip 16, in order to be able to remove the annular inserts 2a together with the casings and the plastic containers suspended therein. In order to be able to suitably suspend the plastic containers, they have at the upper portion a wider rim 21, which is wider than the internal diameter of the casing 4. In the exemplary embodiment shown, there is an upper portion of the casing with a widened internal diameter 22 in order to be able to accommodate a widened rim of a plastic container 21. If the annular insert 2a is removed together with the plastic containers 6, then the wider upper rim of the plastic container makes its way into the corresponding upper recess of the casing with the enlarged internal diameter and is then held particularly securely during transport.

The diameter of the basic body shown in FIG. 1 is about 80 mm. The basic body has a height of about 50 mm. The internal diameter of a metallic casing 4 is 11 mm. Such a casing 4 has a height of 35 mm. Expediently, correspondingly dimensioned plastic containers 6 are filled with about 25 mg of sample material as standard.

The aforementioned dimensions and materials of the adapter are merely expedient and need not be chosen mandatorily. The same applies to the design of the adapter shown.

Figure 2:
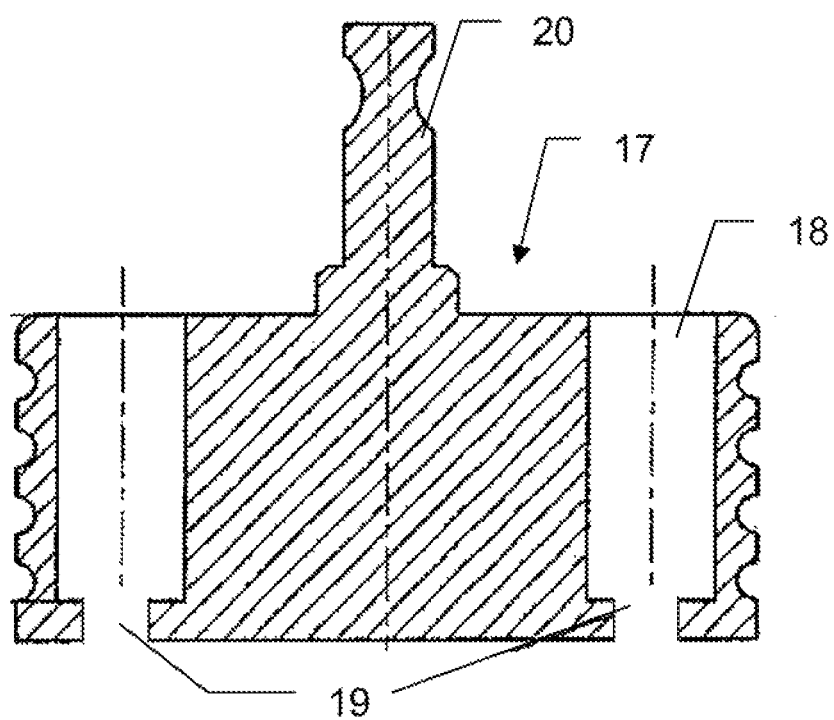

FIG. 2 shows a stand 17 on which the annular insert 2a can be placed together with the suspended plastic containers 6 and casings 4. The cylindrical depressions 18 of the stand serve for accommodating the casings 4 and plastic containers 6. Drill cones 19 serve for pushing out the plastic containers from the casings in order to be able to easily remove the plastic containers. The upwardly protruding grip 20 of the stand 17 is pushed through the central opening of the annular insert 2a in order to place the annular insert 2a on the stand 17.

The following experiments were carried out with the adapter shown in FIG. 1.

1. DNA Isolation from Fresh Rat Liver and Fresh Rat Heart 12 samples (25 mg), respectively, of fresh rat liver and heart were added to 180 μl ATL, that is, a buffer comprising complexing agents and surfactants, commercially available from QIAGEN GmbH, Hilden, Germany, (see webpage http://www1.giagen.com/Products/Accessories/Buffers/BufferAThL.aspx), 10 μl DX (see webpage http://www1.giagen.com/Products/ReagentDX.aspx) and two metallic stainless-steel balls (also referred to as "beads") with a diameter of 5 mm and disrupted at 50 Hz for 1.5 min. Tests showed that turbulences are greater in the case of two beads, which leads to the tissue being ground to a higher degree. Thus, the adapter was moved up and down at a frequency of 50 Hz by the apparatus. The samples were then removed and centrifuged with a small table centrifuge. The adapter was clamped into this table centrifuge after the disruption process. The centrifuge was then switched on for a short period of time in order to bring all constituents to the bottom of the adapter again.

Then, 20 μl Proteinase K was added, vortexing was carried out and the solution was incubated for 1 h 56° C. After incubation, 4 μl RNAse A (100 mg/ml) was added to the sample and incubated for 5 min. Other steps were carried out in accordance with the DNeasy protocol (see webpage http://www1.giagen.com/Products/GenomcDnaStabilizationPurification/DNea syTissueSystem/DNeasyBloodTissueKit.aspx).

Results:

Heart:

The heart tissue yielded an average of 5.83 μg DNA and a standard deviation of 1.07. The isolated DNA quantity could have been slightly higher, but otherwise, there were no complaints.

Liver:

The liver tissue yielded an average of 34.08 μg DNA and a standard deviation of 10.97. The disruption of the liver tissue showed that the disruption works very well.

2. DNA Isolation from Fresh Bovine Liver 12 samples (25 mg), respectively, of fresh bovine liver were added to 180 μl ATL, 6 μl DX and 2 beads and disrupted at 50 Hz for 2 minutes. The samples were then removed and centrifuged. Then, 20 μl Proteinase K was added, vortexing was carried out and the solution was incubated for 1.5 h 56° C. After incubation, 4 μl RNAse A (100 mg/ml) was added to the sample and incubated at room temperature for 5 min. Further steps were carried out according to the tissue and rodent tail protocol on the QIAcube by Quiagen, Hilden, Germany. The tissue and rodent tail protocol is shipped together with the QIA cube.

Results:

Liver:

The liver tissue yielded an average of 44.38 μg DNA and a standard deviation of 12.84. The disruption of the liver tissue again showed that the disruption works very well. DNA was again already visible as a white wad and could be transferred into a new MRV using a pipette only with difficulty (MRV=micro reaction vessel, or "eppi" in short).

As a rule, 20 μg DNA are expected. The high average of 44.38 DNA suggested a progressive degradation of the DNA. Small fragments cause a higher signal in the measurement, which is erroneously indicated as a higher concentration.

The invention claimed is:

1. Method for simultaneously disrupting a plurality of biological samples, comprising the steps of:
    the samples are filled into a plurality of non-metallic containers,
    at least one movable hard body is filled into each container,
    the containers are inserted into an adapter having casings of metal disposed in a circle about a central axis of the adapter wherein the adapter is cooled to between −20° C. and −80° C., and wherein the adapter is not actively cooled during reciprocation,
    the adapter, with the sealed containers located therein, is connected to an apparatus that automatically reciprocates the adapter.

2. Method according to claim 1, wherein the samples are first washed and then frozen with liquid nitrogen or chemically preserved, and the samples thus prepared are filled into the container.

3. Method according to claim 1, wherein the containers, samples and adapter are first cooled to between −20° C. and −80° C., and the sample is subsequently disrupted by reciprocating the adapter.

4. Method according to claim 1, wherein the at least one moveable hard body comprises metal or glass.

5. Method according to claim 1, wherein a lysis buffer is filled into the containers prior to disruption.

6. Method according to claim 1, wherein the adapter is reciprocated at a frequency of at least 10 Hz.

7. Method according to claim 1, wherein the weight of a sample filled into a container is no more than 50 mg.

8. Method according to claim 1, wherein the containers comprise plastic.

9. Device for carrying out a method according to claim 1, comprising an adapter comprising plastic, with casings comprising metal for accommodating non-metallic containers.

10. Device according to claim 9, wherein the adapter is connected detachably, to an apparatus that is capable of automatically reciprocating the adapter parallel to the casings.

11. Device according to claim 10, wherein the apparatus is configured such that it is capable of reciprocating the adapter at a frequency of at least 10 Hz.

12. Device according to claim 9, with containers which are inserted into the casings and in which a biological sample and, additionally, a moveable hard body is located.

13. Device according to claim 9, with an internal casing diameter of the metallic casings of no more than 16 mm.

14. Device according to claim 9, with at least six metallic casings for accommodating containers.

15. Device according to claim 9, wherein the casings are retained by an insert that is removable from the adapter.

16. Device according to claim 9 with casings which, in a top view, are disposed in the shape of a ring.

17. Device according to claim 9, with a lid that can be firmly connected to the adapter.

18. The method of claim 1, wherein said adapter is not actively cooled during reciprocation.

19. The method of claim 5, wherein said lysis buffer comprises a buffer comprising complexing agents and surfactants for disrupting DNA, or a buffer comprising a chaotropic agent for disrupting RNA.

20. The method of claim 1, wherein said adapter consists of plastic.

* * * * *